United States Patent [19]

Weissmüller et al.

[11] Patent Number: 4,542,130
[45] Date of Patent: Sep. 17, 1985

[54] 5-AMINOMETHYL-1,3-OXATHIOLANE MICROBICIDES, COMPOSITIONS AND USE

[75] Inventors: Joachim Weissmüller; Wolfgang Krämer; Dieter Berg, all of Wuppertal; Paul Reinecke, Leverkusen; Wilhelm Brandes, Leichlingen; Gerd Hänssler, Leverkusen, all of Fed. Rep. of Germany

[73] Assignee: Bayer Aktiengesellschaft, Leverkusen, Fed. Rep. of Germany

[21] Appl. No.: 624,889

[22] Filed: Jun. 27, 1984

[30] Foreign Application Priority Data

Jul. 8, 1983 [DE] Fed. Rep. of Germany ....... 3324769

[51] Int. Cl.[4] ................... A01N 43/28; A01N 43/84; C07D 327/04; C07D 413/06
[52] U.S. Cl. .................................. 514/212; 514/230; 514/252; 514/319; 514/326; 514/422; 514/439; 544/145; 544/374; 546/205; 546/206; 546/207; 548/527; 549/30; 260/330.3
[58] Field of Search ................ 544/145, 374; 546/205, 546/206, 207; 548/527; 260/330.3; 549/30; 424/248.51, 250, 267, 274, 276

[56] References Cited

U.S. PATENT DOCUMENTS 4,503,059  3/1985  Kramer et al. ...................... 544/148

Primary Examiner—Robert W. Ramsuer
Attorney, Agent, or Firm—Sprung, Horn, Kramer & Woods

[57] ABSTRACT

MIcrobicidally active 5-aminomethyl-1,3-oxathiolanes of the formula

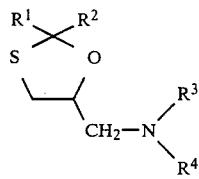

in which
$R^1$ is tetrahydronaphthyl, decahydronaphthyl or optionally substituted naphthyl, optionally substituted cycloalkyl or cycloalkenyl, optionally substituted phenyl, or alkyl which is substituted by phenyl, phenoxy, phenylthio, cyclohexyl, cyclohexyloxy or cyclohexylthio, each of which is optionally substituted,
$R^2$ is hydrogen or methyl,
$R^3$ is alkyl, and
$R^4$ is alkyl, alkenyl or optionally substituted aralkyl, or
$R^3$ and $R^4$, together with the nitrogen atom to which they are bonded, form an optionally substituted saturated heterocyclic structure which can contain further heteroatoms, or a plant-tolerated addition product thereof with an acid or metal salt.

11 Claims, No Drawings

5-AMINOMETHYL-1,3-OXATHIOLANE MICROBICIDES, COMPOSITIONS AND USE

The invention relates to 5-aminomethyl-1,3-oxathiolanes, a process for their preparation and their use as pest-combating agents.

It is already known that organic sulphur compounds, such as, for example, zinc ethylene-1,2-bis-(dithiocarbamate) [see R. Wegler "Chemie der Pflanzenschutzund Schädlingsbekämpfungsmittel" (Chemistry of plant protection agents and pest-combating agents), Springer Verlag, Berlin, Heidelberg, New York 1970, Volume 2, page 65 et seq.], or basic alkylamino compounds, such as, for example, 4-[3-(4-t-butylphenyl)-2-methyl]-propyl-2,6-di-methyl-morpholine (see DE-OS (German Published Specification) No. 2,656,747), possess fungicidal properties.

However, the action of these compounds is not always completely satisfactory in all fields of use, particularly when small amounts and concentrations are used.

New 5-aminomethyl-1,3-oxathiolanes of the general formula (I)

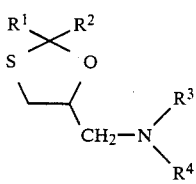

in which $R^1$ reoresents tetrahydronaphthyl, decahydronaphthyl or optionally substituted naphthyl, optionally substituted cycloalkyl and cycloalkenyl, optionally substituted phenyl, or alkyl which is substituted by phenyl, phenoxy, phenylthio, cyclohexyl, cyclohexyloxy or cyclohexylthio, each of which is optionally substituted, $R^2$ represents hydrogen or methyl, $R^3$ represents alkyl and $R^4$ represents alkyl, alkenyl or optionally substituted aralkyl, or $R^3$ and $R^4$, together with the nitrogen atom to which they are bonded, represent an optionally substituted saturated heterocyclic structure which can contain further heteroatoms, and their plant-tolerated acid addition salts and metal salt complexes, have been found.

The compounds of the formula (I) may be obtained as geometric and/or optical isomers or isomer mixtures of differing composition. Both the pure isomers and the isomer mixtures are claimed in accordance with the invention.

Furthermore, it has been found that the 5-aminomethyl-1,3-oxathiolanes of the formula (I) are obtained if 1,3-oxathiolanes which are substituted in the 5-position, of the general formula (II)

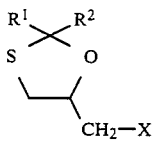

in which $R^1$ and $R^2$ have the meaning given above and X represents halogen or optionally substituted alkylsulphonyloxy or arylsulphonyloxy, are reacted with amines of the general formula (III)

in which $R^3$ and $R^4$ have the meaning given above, if appropriate in the presence of a diluent and, if appropriate, in the presence of a catalyst and, if appropriate, in the presence of an acid-binding agent, and, if required, the product is then subjected to an addition reaction with an acid or a metal salt.

Furthermore, it is possible to quaternize the 5-aminomethyl-1,3-oxathiolanes according to the invention, on the nitrogen atom, by generally customary methods to give the corresponding tetrasubstituted ammonium salts.

The new 5-aminomethyl-1,3-oxathiolanes of the formula (I) have, in particular, fungicidal properties. In this respect, the compounds according to the invention, of the formula (I), surprisingly exhibit higher fungicidal activity than the compounds zinc ethylene-1,2-bis-(dithiocarbamate) or 4-[3-(4-t-butylphenyl)-2-methyl]-propyl-2,6-dimethyl-morpholine, which are known from the prior art and are compounds having the same direction of action. The compounds according to the invention thus represent an enrichment of the art.

Formula (I) gives a general definition of the 5-aminomethyl-1,3-oxathiolanes according to the invention.

Preferred compounds of the formula (I) are those in which $R^1$ represents tetrahydronaphthyl or decahydronaphthyl, or represents naphthyl which is optionally monosubstituted or polysubstituted by identical or different substituents, suitable substituents being: hydroxyl or halogen, or alkyl, alkoxy, alkenyloxy, alkinyloxy or alkanoyloxy, each of which is straight-chain or branched and has up to 4 carbon atoms in the alkyl parts, and furthermore represents cycloalkyl or cycloalkenyl, each of which has 3 to 7 carbon atoms and is optionally monosubstituted or polysubstituted by identical or different straight-chain or branched alkyl radicals having up to 4 carbon atoms, or represents phenyl which is optionally monosubstituted or polysubstituted by identical or different substituents, or represents phenylalkyl, phenoxyalkyl or phenylthioalkyl, each of which is optionally monosubstituted or polysubstituted in the phenyl nucleus by identical or different substituents and has up to 6 carbon atoms in the straight-chain or branched alkyl part, suitable phenyl substituents in each case being: hydroxyl, halogen, cyano or nitro, or alkyl, alkoxy, alkenyloxy, alkinyloxy and alkylthio, each of which is straight-chain or branched and has up to 4 carbon atoms, halogenoalkyl, halogenoalkoxy and halogenoalkylthio, each of which has 1 or 2 carbon atoms and 1 to 5 identical or different halogen atoms, cycloalkyl having 5 to 7 carbon atoms, straight-chain or branched alkoxycarbonyl or alkanoyloxy, each of which has up to 4 carbon atoms in the alkyl part, phenyl or phenoxy which is optionally substituted by halogen, in particular fluorine or chlorine, or by straight-chain or branched alkyl having up to 4 carbon atoms, and the radical R—O—N=CH—, wherein R in each case represents straight-chain or branched alkyl, alkenyl or alkinyl having up to 4 carbon atoms; furthermore, cyclohexylalkyl, cyclohexyloxyalkyl or cyclohexylthioalkyl, each of which has up to 6 carbon atoms in the straight-chain or branched alkyl parts and is optionally monosubstituted or polysubstituted in the cyclohexyl part by identical or different straight-chain or branched alkyl radicals having up to 4 carbon atoms, $R^2$ represents hydrogen or methyl, $R^3$ represents straight-chain or branched alkyl having up to 4 carbon atoms and $R^4$ represents straight-chain or branched alkyl having up to 4 carbon atoms, straight-chain or branched alkenyl having up to 6 carbon atoms or aralkyl which is optionally monosubstituted or polysubstituted by identical or different substituents and has 1 or 2 carbon atoms in the alkyl part and 6 to 10 carbon atoms in the aryl part, suitable aryl substituents in each case being: halogen, straight-chain or branched alkyl having up to 4 carbon atoms and halogenoalkyl having 1 or 2 carbon atoms and up to 5 identical or different halogen atoms, or $R^3$ and $R^4$, together with the nitrogen atom to which they are bonded, represent the 5-membered to 7-membered saturated heterocyclic structure which is optionally monosubstituted or polysubstituted by identical or different substituents and has 1 to 3 heteroatoms, preferably nitrogen or oxygen, suitable substituents being: straight-chain or branched alkyl having up to 4 carbon atoms, straight-chain or branched alkoxycarbonyl having up to 5 carbon atoms, phenyl, hydroxymethyl and the R'—CO—O—CH$_2$ group, wherein R' represents straight-chain or branched alkyl, alkoxy or alkylamino or dialkylamino, each having 1 to 6 carbon atoms in the individual alkyl parts, or straight-chain or branched alkoxyalkyl, each having 1 to 6 carbon atoms in the two alkyl parts, or represents the furyl radical.

Particularly preferred compounds are those of the general formula (I), in which $R^1$ represents tetrahydronaphthyl or decahydronaphthyl, or represents naphthyl which is optionally monosubstituted to trisubstituted by identical or different substituents, suitable substituents being: fluorine, chlorine, bromine, iodine, hydroxyl, methyl, ethyl, methoxy, ethoxy, allyloxy, propargyloxy and acetoxy, and furthermore represents cycloalkyl or cycloalkenyl, each of which is optionally monosubstituted to trisubstituted by identical or different substituents from amongst methyl and ethyl and has 5 to 7 carbon atoms, or represents phenyl which is optionally monosubstituted to trisubstituted by identical or different substituents, or represents a radical of the formula

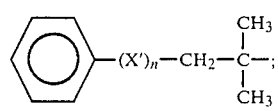

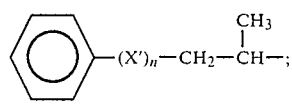

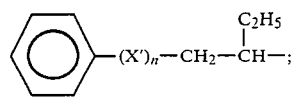

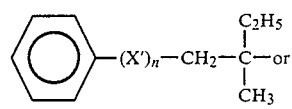

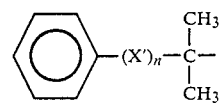

which is optionally monosubstituted to trisubstituted in the phenyl nucleus by identical or different substituents, suitable phenyl substituents in each case being: hydroxyl, fluorine, chlorine, bromine, iodine, cyano, nitro, methyl, methoxy, methylthio, ethylthio, ethoxy, ethylthio, n- and i-propyl, isopropoxy, n-, i-, s- and t-butyl, allyloxy, propargyloxy, trifluoromethyl, trifluoromethoxy, trifluoromethylthio, cyclohexyl, methoxycarbonyl, ethoxycarbonyl and acetoxy, and phenoxy or phenyl which is optionally substituted by fluorine, chlorine or methyl, and the radical R—O—N=CH—, wherein R in each case represents methyl, ethyl, n- and i-propyl, n-, i-, s- and t-butyl, allyl and propargyl; and furthermore represents a radical of the formula

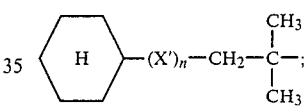

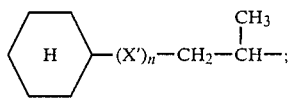

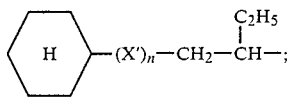

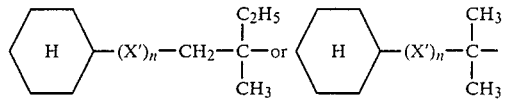

which is optionally monosubstituted to trisubstituted in the cyclohexyl part by identical or different substituents from amongst methyl, ethyl and isopropyl, and in all of the radicals represented above as formulae X' in each case represents oxygen or sulphur and n represents 0 or 1, $R^2$ represents methyl, $R^3$ represents methyl, ethyl, n- and i-propyl and $R^4$ represents methyl, ethyl, n- and i-propyl, n-, i-, s- and t-butyl, allyl, but-2-enyl and 3-methylbut-2-enyl, and represents benzyl which is optionally monosubstituted to trisubstituted by identical or different substituents from amongst fluorine, chlorine, methyl and trifluoromethyl, or $R^3$ and $R^4$, together with the nitrogen atom to which they are bonded, represent pyrrolidin-1-yl, piperid-1-yl, piperazin-1-yl, morpholin-4-yl or 1-perhydroazepinyl, each of which is optionally monosubstituted to trisubstituted by identical or different substituents, the following being mentioned as substituents: methyl, ethyl, n- and i-propyl, phenyl, hydroxymethyl, acetoxymethyl, methoxycarbonyloxymethyl, dimethylaminocarbonyloxymethyl, diethylaminocarbonyloxymethyl, methoxyacetoxymethyl or furoyloxymethyl. In addition to the compounds mentioned in the preparation examples, the following compounds of the general formula (I) may be mentioned individually:

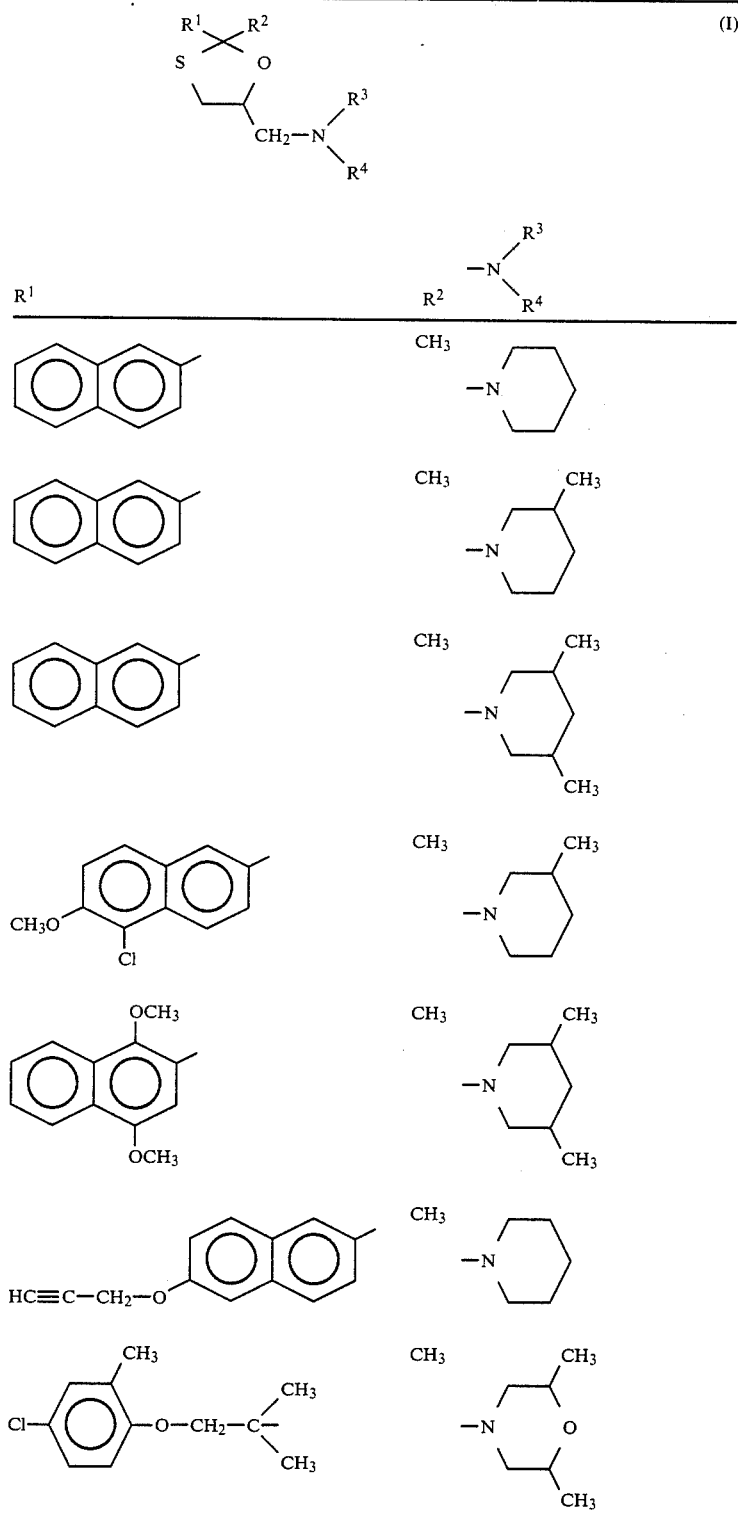

-continued
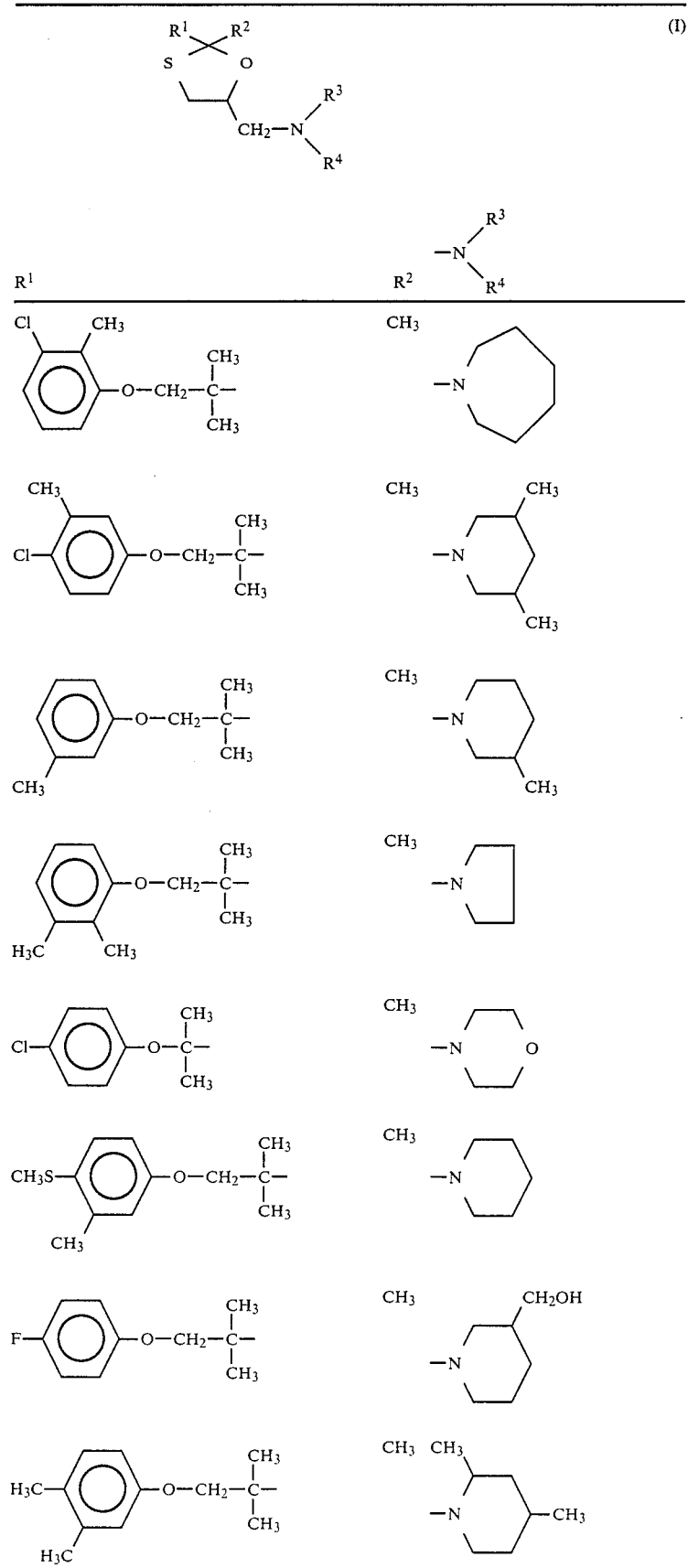

-continued
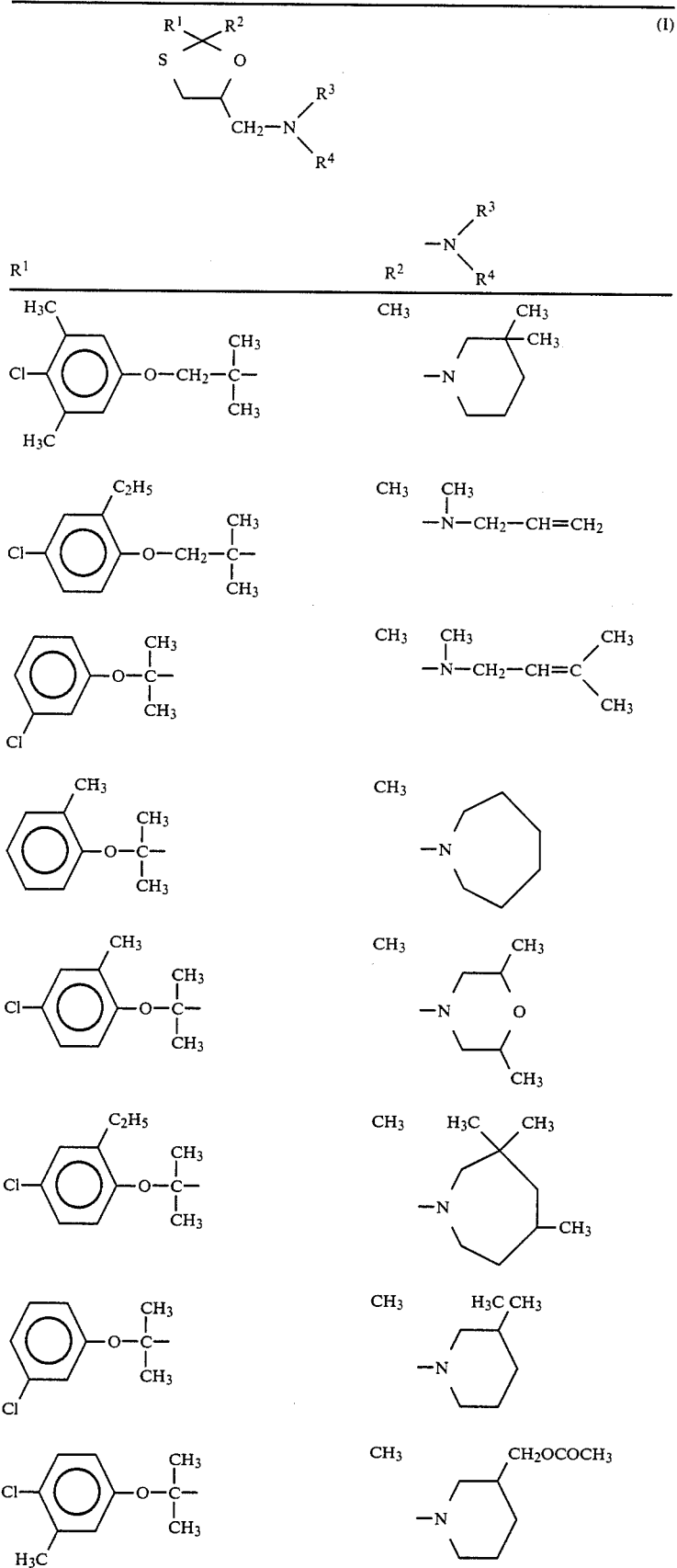

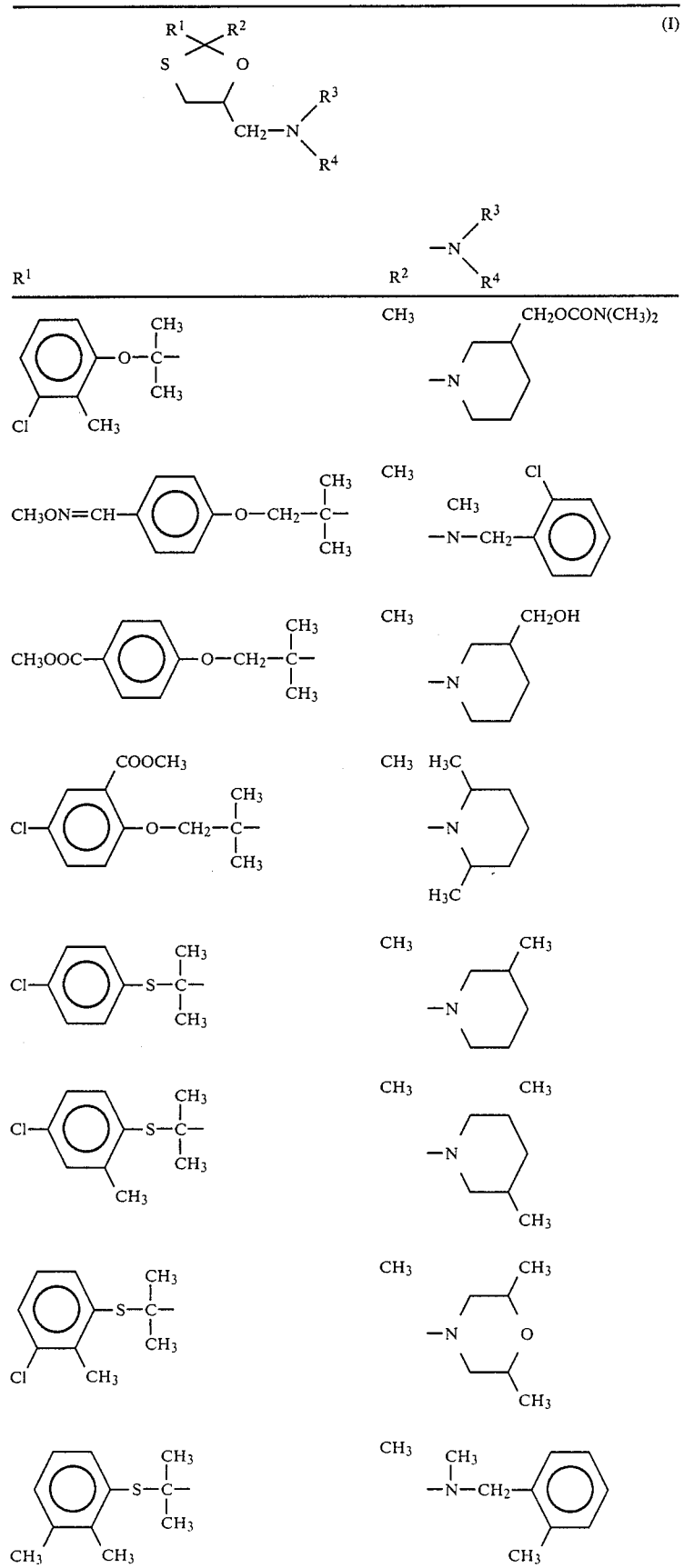

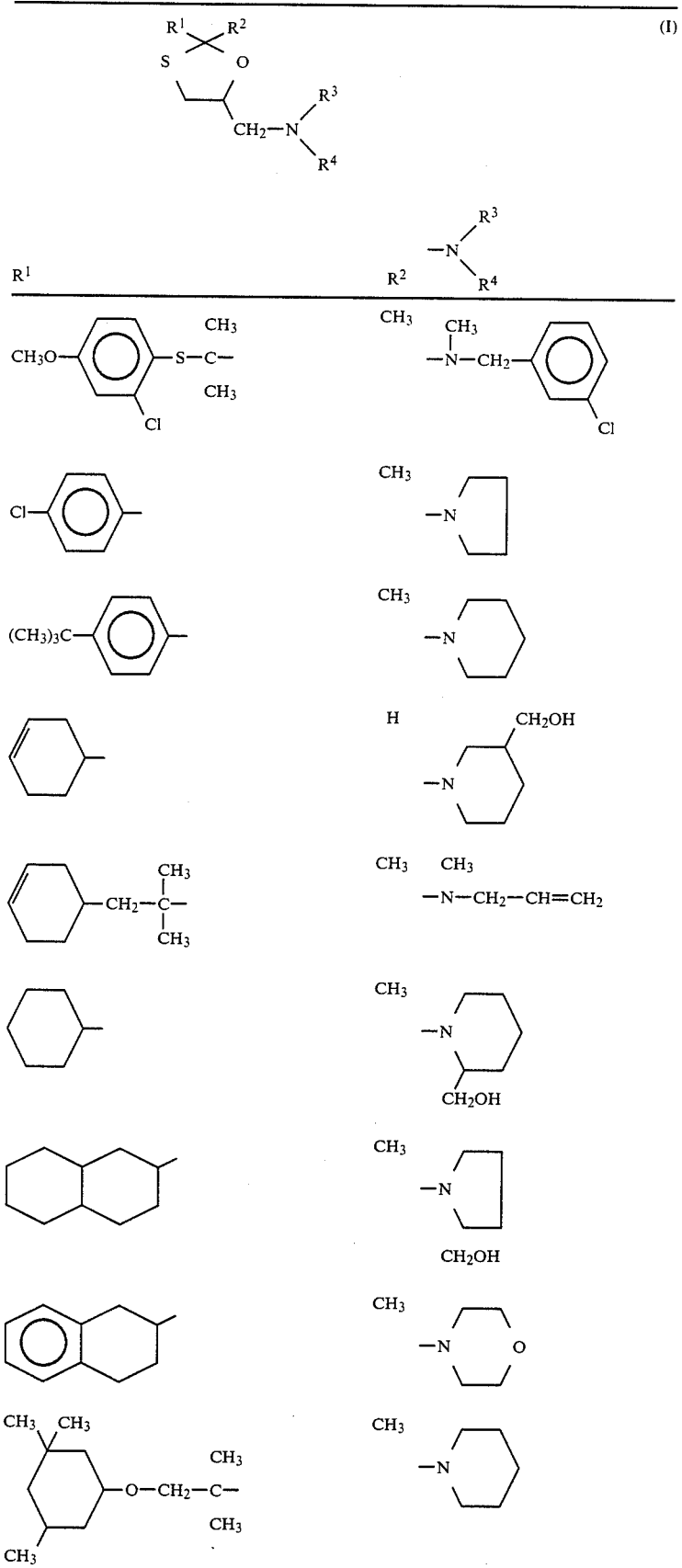

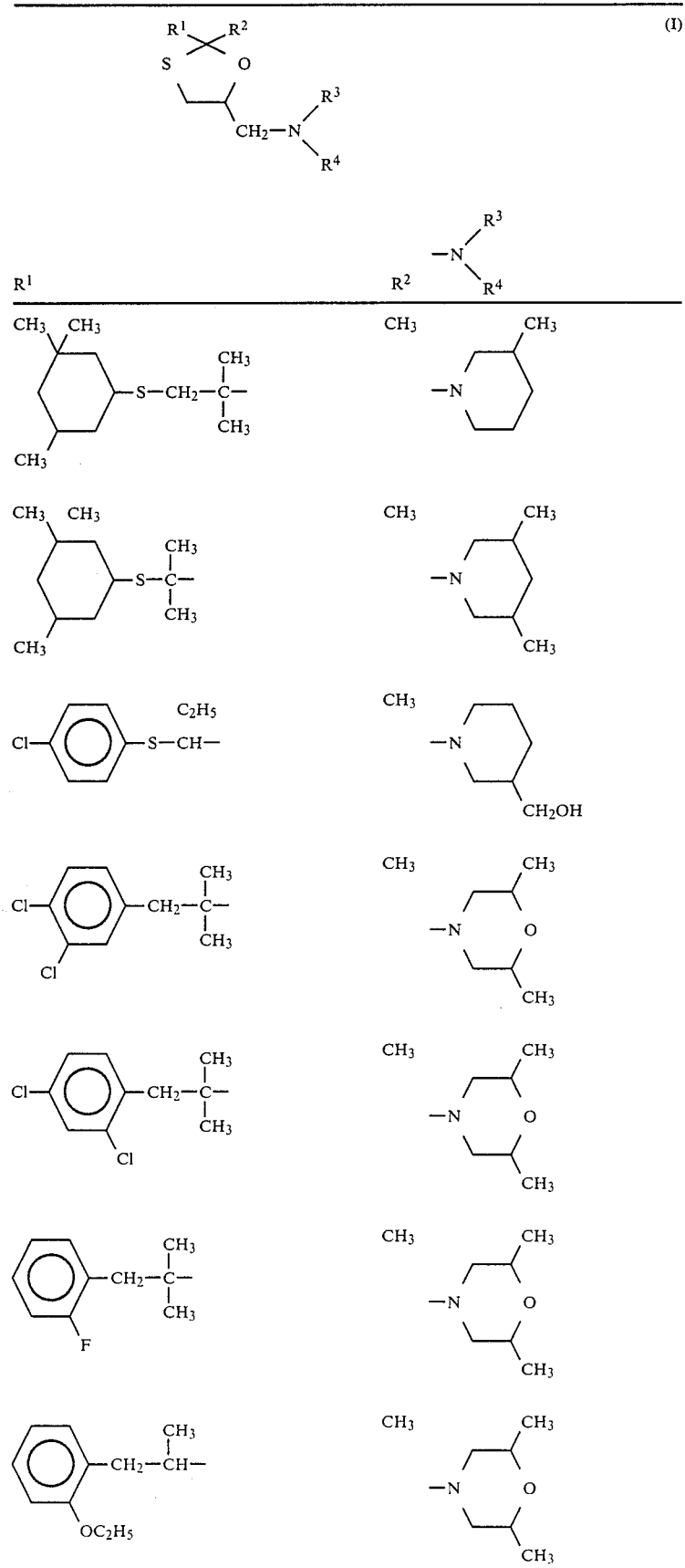

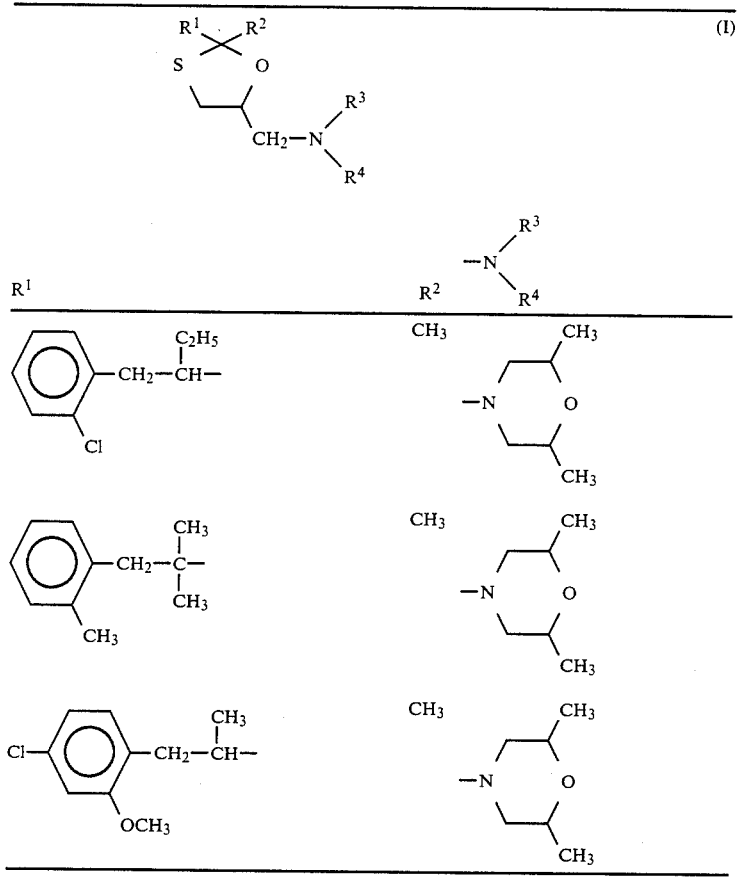

If, for example, 5-chloromethyl-2-[1-(4-chlorophenoxy)-2-methyl]-prop-2-yl-2-methyl-1,3-oxathiolane and piperidine are used as starting materials, the course of the reaction of the process according to the invention can be represented by the following equation:

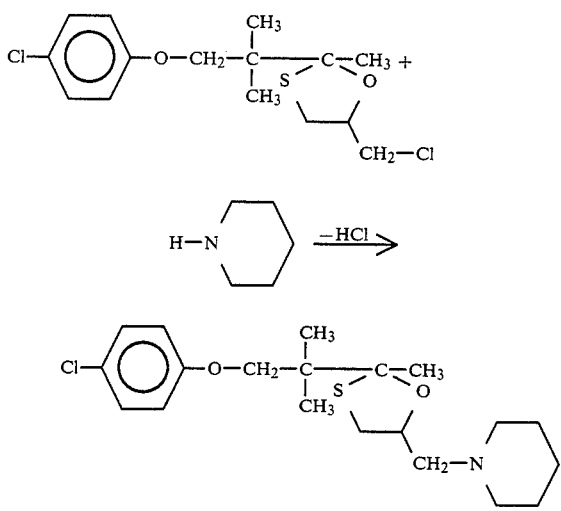

Formula (II) gives a general definition of the 1,3-oxathiolanes which are substituted in the 5-position and are required as starting materials for carrying out the process according to the invention. In this formula, $R^1$ and $R^2$ preferably have the same meaning which are given as prepared in the description of the compounds according to the invention, of the formula (I), and X preferably represents chlorine, bromine, methanesulphonyloxy, trifluoromethanesulphonyloxy or p-toluenesulphonyloxy.

Some of the 1,3-oxathiolanes substituted in the 5-position, of the formula (II), are known (see Tetrahedron Letters 23, 47–50 [1982]).

Compounds which are not yet known are those of the formula (IIa)

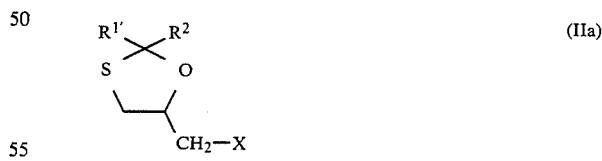

in which $R^{1'}$ represents tetrahydronaphthyl, decahydronaphthyl or optionally substituted naphthyl, optionally substituted cycloalkyl, substituted phenyl, or alkyl which is substituted by phenyl, phenoxy, phenylthio, cyclohexyl, cyclohexyloxy or cyclohexylthio, each of which is optionally substituted, $R^2$ represents hydrogen or methyl, and X represents halogen or optionally substituted alkylsulphonyloxy or arylsulphonyloxy.

The compounds of the formula (IIa) are obtained, in a manner which is known in principle, if aldehydes or ketones of the formula (IV)

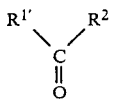

in which

R$^{1'}$ and R$^2$ have the meaning given above, are reacted with thiopropanol derivatives of the formula (V)

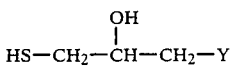

in which

Y represents halogen or hydroxyl, if appropriate in the presence of a diluent, such as, for example, diethyl ether, and, if appropriate, in the presence of a catalyst, such as, for example, boron trifluoride, at temperatures between 0° C. and 120° C., and in the cases where Y represents the hydroxyl group, the resulting 5-hydroxymethyl-1,3-oxathiolanes of the formula (IIb)

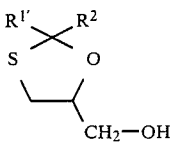

in which

R$^{1'}$ and R$^2$ have the meaning given above, are reacted with optionally substituted alkyl- or arylsulphonyl halides of the formula (VI)

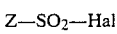

in which

Hal represents halogen, preferably chlorine, and

Z represents optionally substituted alkyl or aryl, preferably methyl, trifluoromethyl or 4-methylphenyl, if appropriate in the presence of a diluent, such as, for example, diethyl ether, and, if appropriate, in the presence of an acid-binding agent, such as, for example, pyridine or triethylamine, at temperatures between −20° C. and +100° C., to give the compounds of the formula (IIc)

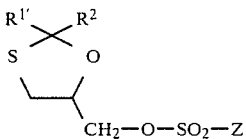

in which

R$^{1'}$, R$^2$ and Z have the meaning given above.

Ketones of the formula (IV) are known (see, for example, DE-OS (German Published Specification) No. 3,210,725 or DE-OS (German Published Specification) No. 3,048,266), and can be obtained in a simple manner by known methods.

The thiopropanol derivatives of the formula (V) and the sulohonyl halides of the formula (VI) are generally known compounds of organic chemistry.

Formula (III) gives a general definition of the amines furthermore required as starting materials for the process according to the invention. In this formula, R$^3$ and R$^4$ preferably represent those radicals which have already been mentioned in connection with the description of the substances according to the invention, of the formula (I), as being preferred for these substituents.

The amines of the formula (III) are generally known compounds of organic chemistry.

The process according to the invention can, if appropriate, be carried out in the presence of a diluent. Suitable diluents are inert organic solvents. These preferably include aromatic hydrocarbons, such as benzene, toluene or xylene; halogenated hydrocarbons, such as carbon tetrachloride or chlorobenzene; formamides, such as dimethylformamide; nitriles, such as acetonitrile or propionitrile; alcohols, such as propanol or butanol; amines, such as triethylamine or piperidine; and the highly polar solvents dimethyl sulphoxide or hexamethylphosphoric acid triamide.

The process according to the invention is, if appropriate, carried out in the presence of a base as an acid-binding agent. All customary organic and inorganic bases can be employed. These preferably include alkali metal hydroxides or carbonates, such as, for example, sodium hydroxide, sodium carbonate or potassium carbonate; and furthermore triethylamine and pyridine. If required, the amines of the formula (III) which are employed as starting materials can also be used as diluents and as acid-binding agents.

The process according to the invention is, if appropriate, carried out in the presence of a catalyst. Alkali metal iodides, such as, for example, potassium iodide, are preferably used.

In the process according to the invention, the reaction temperatures can be varied within a relatively wide range. In general, the reaction is carried out at between 50° C. and 250° C., preferably between 80° C. and 200° C.

The process according to the invention can be carried out under atmospheric pressure, as well as under elevated pressure. Where pressure is employed, the reaction is carried out in general under between about 1.5 atm gauge pressure and 5 atm gauge pressure, preferably between 1.5 atm gauge pressure and 3 atm gauge pressure.

In carrying out the process according to the invention, 1 to 30 mols of the amine of the formula (III) are preferably employed per mol of the substituted oxathiolane of the formula (II), depending on whether the amine is also used as a diluent and/or acid-binding agent. The end products are isolated by customary methods.

For the preparation of plant-tolerated acid addition salts of the compounds of the formula (I), the following acids are preferred: hydrohalic acids, such as, for example, hydrochloric acid and hydrobromic acid, in particular hydrochloric acid, and furthermore phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid or lactic acid, and sulphonic acids, such as, for example, p-toluenesulphonic acid and naphthalene-1,5-disulphonic acid. The acid addition salts of the compounds of the formula (I) can be obtained in a simple manner by customary salt formation methods, for example by dissolving a compound of the formula (I) in a suitable inert solvent and adding the acid, for example hydrochloric acid, and can be isolated in a known manner, for example by filtration, and, if required, purified by washing with an inert organic solvent.

Preferred salts for the preparation of metal salt complexes of the compounds of the formula (I) are salts of metals of main group II to IV and of sub-group I or II and IV to VIII, copper, zinc, manganese, magnesium, tin, iron and nickel being mentioned as examples. Suitable anions of the salts are those which are preferably derived from the following acids: hydrohalic acids, such as, for example, hydrochloric acid and hydrobromic acid, and also phosphoric acid, nitric acid and sulphuric acid.

The metal salt complexes of compounds of the formula (I) can be obtained in a simple manner by customary processes, thus, for example, by dissolving the metal salt in alcohol, for example ethanol, and adding the solution to the compound of the formula (I). Metal salt complexes can be isolated in a known manner, for example by filtration, and, if required, purified by recrystallization.

The active compounds according to the invention exhibit a powerful microbicidal action and can be employed in practice for combating undesired microorganisms. The active compounds are suitable for use as pest-combating agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as, for examole, against the powdery mildew of barley causative organism (Erysiphe graminis) or against the stripe disease of barley causative organism (Drechslera graminea), rice diseases, such as, for example, against the blast disease of rice causative organism (Pyricularia oryzae), or fruit and vegetable diseases, such as, for example, against the apple scab causative organism (Venturia inaequalis) or against the grey mold of bean causative organism (Botrytis cinerea). The active compounds according to the invention possess both protective and systemic activity.

Moreover, they also have a good action against the cereal disease causative organisms Septoria nodorum, Cochliobolus sativus and Pyrenophora teres, against the rice disease causative organism Pellicularia sasakii, against Oomycetes and against powdery mildew fungi. In addition, the active compounds according to the invention also have a good in vitro fungicidal action.

The active compounds can be converted to the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strong polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

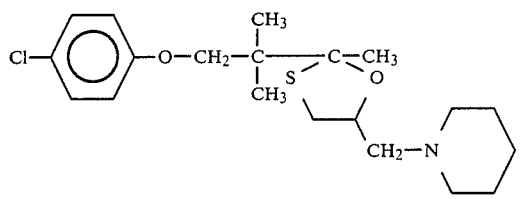

10 g (0.03 mol) of 5-chloromethyl-2-[1-(4-chlorophenoxy- 2-methyl]-prop-2-yl-2-methyl-1,3-oxathiolane and 10 g (0.12 mol) of piperidine are heated to 120° C. for 12 hours. After cooling, the reaction mixture is diluted with ethyl acetate, washed twice with water, dried over sodium sulphate and evaporated down in vacuo. The residue is subjected to distillation in a ball tube (b.p.: ~200° C./0.13 mbar) or is chromatographed over a silica gel column, using a 2:1 petroleum ether-/ethyl acetate mixture as the mobile phase. 8 g (69.5% of theory) of 2-(1-[4-chlorophenoxy)-2-methyl]-prop-2-yl-2-methyl-5-piperid-1-ylmethyl-1,3-oxathiolane of refractive index $n_D^{20}=1.5440$ are obtained.

The compounds of the general formula (I)

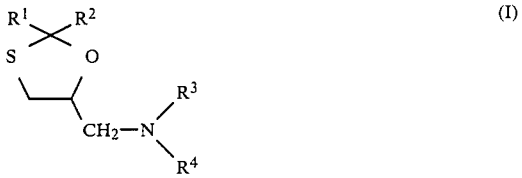

which are listed below are obtained in a corresponding manner and in accordance with the general data for the preparation:

| Example Number | $R^1$ | $R^2$ | $-N\begin{matrix}R^3\\R^4\end{matrix}$ | Refractive index $[n_D^{20}]$ |
|---|---|---|---|---|
| 2 | 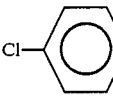 | CH$_3$ | 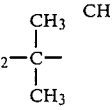 | 1.5382 |
| 3 | 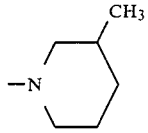 | CH$_3$ | 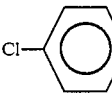 | 1.5331 |
| 4 | 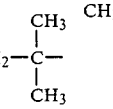 | CH$_3$ | 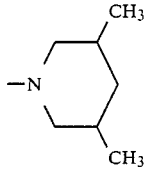 | 1.5357 |
| 5 | 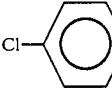 | CH$_3$ | 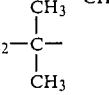 | 1.5341 |
| 6 |  | CH$_3$ | 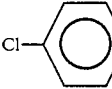 | 1.5039 |

-continued

| Example Number | R¹ | R² | —N(R³)(R⁴) | |
|---|---|---|---|---|
| 7 | 4-Cl-C₆H₄-O-CH₂-C(CH₃)₂- | CH₃ | -N(piperazine)N-CH₃ | 1.5065 |
| 8 | 4-Cl-C₆H₄-O-CH₂-C(CH₃)₂- | CH₃ | -N(piperazine)N-C₆H₅ | 1.5147 |
| 9 | 4-Cl-C₆H₄-O-CH₂-C(CH₃)₂- | CH₃ | -N(pyrrolidine) | 1.5007 |
| 10 | 4-Cl-C₆H₄-O-CH₂-C(CH₃)₂- | CH₃ | 3-(CH₂OH)-piperidin-1-yl | 1.5077 |
| 11 | 3-Cl-C₆H₄-O-CH₂-C(CH₃)₂- | CH₃ | 3-CH₃-piperidin-1-yl | 1.5082 |
| 12 | 3-Cl-C₆H₄-O-CH₂-C(CH₃)₂- | CH₃ | 3,5-diCH₃-piperidin-1-yl | 1.5049 |
| 13 | 3-Cl-C₆H₄-O-CH₂-C(CH₃)₂- | CH₃ | piperidin-1-yl | 1.5058 |
| 14 | 2,4-diCl-C₆H₃-O-CH₂-C(CH₃)₂- | CH₃ | piperidin-1-yl | 1.5091 |
| 15 | 2,4-diCl-C₆H₃-O-CH₂-C(CH₃)₂- | CH₃ | 3-CH₃-piperidin-1-yl | 1.5077 |
| 16 | 2,4-diCl-C₆H₃-O-CH₂-C(CH₃)₂- | CH₃ | 3,5-diCH₃-piperidin-1-yl | 1.5069 |

-continued

| Example Number | R¹ | R² | —N(R³)(R⁴) | |
|---|---|---|---|---|
| 17 | 2,4-dichlorophenyl-O—CH₂—C(CH₃)₂— | CH₃ | 3,3-dimethylpiperidin-1-yl | 1.5087 |
| 18 | 2,4-dichlorophenyl-O—CH₂—C(CH₃)₂— | CH₃ | 4-methylpiperidin-1-yl | 1.5083 |
| 19 | 2,4-dichlorophenyl-O—CH₂—C(CH₃)₂— | CH₃ | hexamethyleneimin-1-yl (azepan-1-yl) | 1.5110 |
| 20 | 4-fluorophenyl-CH₂—C(CH₃)₂— | CH₃ | 3-methylpiperidin-1-yl | 1.5245 |
| 21 | 2-methylphenyl-O—CH₂—C(CH₃)₂— | CH₃ | 3,3-dimethylpiperidin-1-yl | 1.5070 |
| 22 | 2-methylphenyl-O—CH₂—C(CH₃)₂— | CH₃ | hexamethyleneimin-1-yl | 1.5062 |
| 23 | 2-methylphenyl-O—CH₂—C(CH₃)₂— | CH₃ | 3,3-dimethyl-5-methylene-hexahydroazepin-1-yl | 1.5078 |
| 24 | 2-ethylphenyl-O—CH₂—C(CH₃)₂— | CH₃ | 3-methylpiperidin-1-yl | 1.5122 |
| 25 | 2-ethylphenyl-O—CH₂—C(CH₃)₂— | CH₃ | 3-(hydroxymethyl)piperidin-1-yl | 1.5047 | melting point [°C.]

-continued

| Example Number | R¹ | R² | $-N\begin{smallmatrix}R^3\\R^4\end{smallmatrix}$ | |
|---|---|---|---|---|
| 26 | 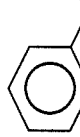 | CH₃ | 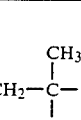 | 1.5086 (cis-form) |
| 27 |  | CH₃ | 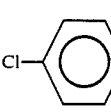 | 1.5039 (cis-form) |
| 28 | 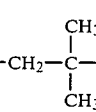 | CH₃ | 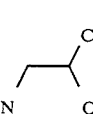 | 179–180 iodide |
| 29 | 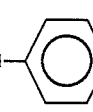 | CH₃ | 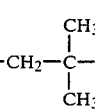 | oil |

PREPARATION OF THE STARTING COMPOUNDS

EXAMPLE II-1

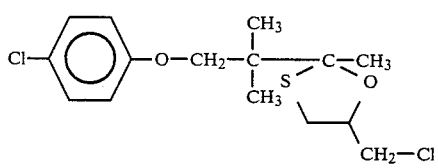

50 g (0.35 mol) of boron trifluoride etherate are added dropwise to a boiling solution of 80.7 g (0.35 mol) of 4-(4-chlorophenoxy)-3,3-dimethyl-butan-2-one and 45 g (0.35 mol) of 1-chloro-3-mercapto-propan-2-ol in 240 ml of absolute ether. After the addition is complete, the mixture is boiled under reflux for a further 90 minutes. The cooled reaction mixture is washed with twice 100 ml of 0.1 molar sodium bicarbonate solution and once with saturated sodium chloride solution, dried over sodium sulphate and freed in vacuo from the solvent. The residue is distilled in vacuo. 50 g (43% of theory) of 5-chloromethyl-2-[1-(4-chlorophenoxy)-2-methyl]-prop-2-yl-2-methyl-1,3-oxathiolane of boiling point 160° C. under 0.3 mbar are obtained.

The following compounds of the general formula (II)

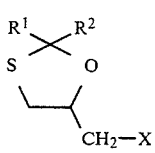 (II)

are obtained in a corresponding manner:

EXAMPLE II-2

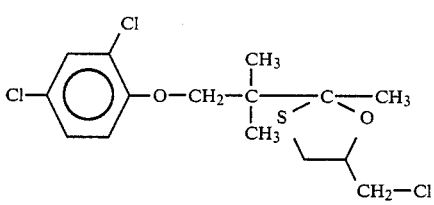

Boiling point: 200° C. under 0.13 mbar

EXAMPLE II-3

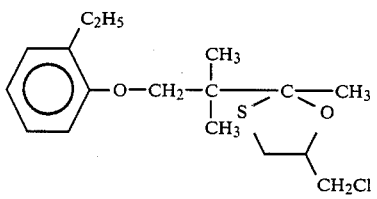

Boiling point: 170° C. under 0.13 mbar

EXAMPLE II-4

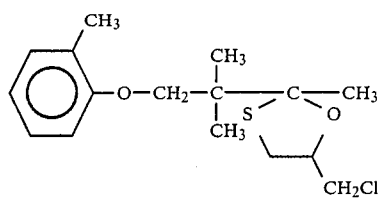

Boiling point: 165°–170° C. under 0.13 mbar

EXAMPLE II-5

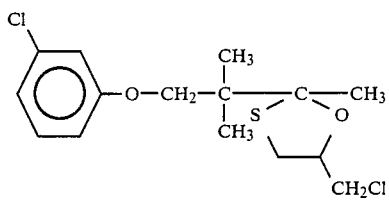

Boiling point: 165°–190° C. under 0.26 mbar (Ball tube distillation at 210° C.)

EXAMPLE II-6

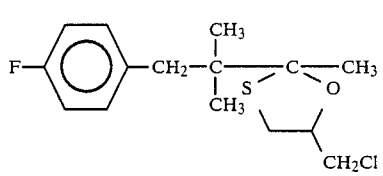

Boiling point: 144° C. under 0.13 mbar

USE EXAMPLES

In the following use examples, the compounds stated below are employed as comparative substances:

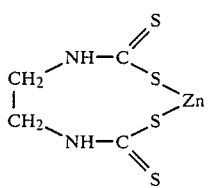
(A)

Zinc ethylene-1,2-bis-(dithiocarbamate)

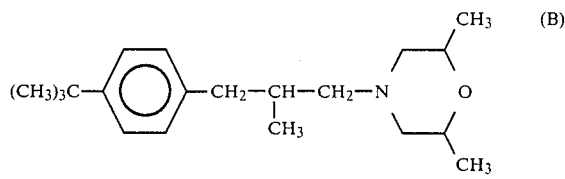
(B)

4[3-(4-t-Butylphenyl)-2-methyl]-prop-1-yl-2,6-dimethylmorpholine

EXAMPLE A

Erysiphe test (barley)/protective/Solvent: 100 parts by weight of dimethylformamide Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the following preparation examples: 1, 2, 3, 4, 5, 6, 7, 11, 12, 14, 15, 16, 17, 18, 19, 21, 22 and 23.

EXAMPLE B

*Drechslera graminea* test (barley)/seed treatment (syn. *Helminthosporium gramineum*)

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

The seed is embedded in sieved, moist standard soil and is exposed to a temperature of 4° C. in closed Petri dishes in a refrigerator for 10 days. Germination of the barley, and possibly also of the fungus spores, is thereby initiated. 2 batches of 50 grains of the pregerminated barley are subsequently sown 3 cm deep in standard soil and are cultivated in a greenhouse at a temperature of about 18° C., in seedboxes which are exposed to light for 15 hours daily.

About 3 weeks after sowing, the plants are evaluated for symptoms of stripe disease.

In this test, a clearly superior activity compared with the prior art is shown, for example, by the compounds according to the following preparation examples: 1 and 2.

EXAMPLE C

Venturia test (apple)/protective/Solvent: 4.7 parts by weight of acetone Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to the following preparation examples: 1, 3, 5, 6 and 22.

EXAMPLE D

Botrytis test (bean)/protective Solvent: 4.7 parts by weight of acetone Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humidity chamber at 20° C. 3 days after the inoculation, the size of the infected spots on the leaves is evaluated.

In this test, a clearly superior activity compared with the prior art is shown, for example, by the compounds according to the following preparation examples: 5, 6, 14, 15, 18 and 19.

EXAMPLE E

Pyricularia test (rice)/systemic Solvent: 12 5 parts by weight oF acetone Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples: 2, 3, 4 and 23.

It is understood that the specification and examples are illustrative but not limitative of the present invention and that other embodiments within the spirit and scope of the invention will suggest themselves to those skilled in the art.

We claim:

1. A 5-aminomethyl-1,3-oxathiolane of the formula

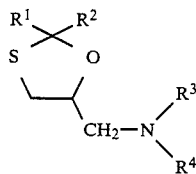

in which $R^1$ is tetrahydronaphthyl, decahydronaphthyl or optionally substituted naphthyl, optionally substituted cycloalkyl or cycloalkenyl, optionally substituted phenyl, or alkyl which is substituted by phenyl, phenoxy, phenylthio, cyclohexyl, cyclohexyloxy or cyclohexylthio, each of which is optionally substituted, $R^2$ is hydrogen or methyl, $R^3$ is alkyl, and $R^4$ is alkyl, alkenyl or optionally substituted aralkyl, or $R^3$ and $R^4$, together with the nitrogen atom to which they are bonded, form an optionally substituted saturated heterocyclic structure which can contain further heteroatoms, or a plant-tolerated addition product thereof with an acid or metal salt, 2. A compound or addition product according to claim 1, in which $R^1$ is tetrahydronaphthyl, decahydronaphthyl or naphthyl, it being possible for the latter to be substituted by hydroxyl, halogen or alkyl, alkoxy, alkenyloxy, alkinyloxy or alkanoyloxy each of which has up to 4 carbon atoms in the alkyl part; or is cycloalkyl or cycloalkenyl each of which has 3 to 7 carbon atoms and is optionally monosubstituted or polysubstituted by identical or different alkyl radicals having up to 4 carbon atoms, or represents optionally substituted phenyl, or is phenylalkyl, phenoxyalkyl or phenylthioalkyl each of which is optionally substituted in the phenyl nucleus and has up to 6 carbon atoms in the alkyl part, the following being mentioned in each case as phenyl substituents: hydroxyl, halogen, cyano, nitro or alkyl, alkoxy, alkenyloxy, alkinyloxy or alkylthio each of which has up to 4 carbon atoms halogenoalkyl, halogenoalkoxy or halogenoalkylthio each of which has 1 or 2 carbon atoms and 1 to 5 identical or different halogen atoms, cycloalkyl having 5 to 7 carbon atoms, alkoxycarbonyl or alkanoyloxy each of which has up to 4 carbon atoms in the alkyl part, phenyl or phenoxy which is optionally substituted by halogen or by alkyl having up to 4 carbon atoms, or the radical R—O—N=CH—, wherein R in each case is alkyl, alkenyl or alkinyl having up to 4 carbon atoms; or is cyclohexylalkyl, cyclohexyloxyalkyl or cyclohexylthioalkyl each of which has up to 6 carbon atoms in the alkyl part and is optionally substituted in the cyclohexyl part by alkyl having up to 4 carbon atoms, $R^3$ is alkyl having up to 4 carbon atoms, and $R^4$ is alkyl having up to 4 carbon atoms, alkenyl having up to 6 carbon atoms or optionally substituted aralkyl having 1 or 2 carbon atoms in the alkyl part and 6 to 10 carbon atoms in the aryl part, the following being mentioned as aryl substituents in each case: halogen, alkyl having up to 4 carbon atoms, and halogenoalkyl having 1 or 2 carbon atoms and up to 5 identical or different halogen atoms or, $R^3$ and $R^4$, together with the nitrogen atom to which they are bonded, form an optionally substituted 5-membered to 7-membered saturated heterocyclic structure having 1 to 3 heteroatoms, the following being mentioned as substituents: alkyl having up to 4 carbon atoms, alkoxycarbonyl having up to 5 carbon atoms, phenyl, hydroxymethyl or the R'—CO—O—$CH_2$ group, wherein R' is alkyl, alkoxy or alkylamino or dialkylamino each having 1 to 6 carbon atoms in the individual alkyl parts, alkoxyalkyl having in each case 1 to 6 carbon atoms in the two alkyl parts, or the furyl radical.

3. A compound or addition product according to claim 1, in which

R¹ is tetrahydronaphthyl, decahydronaphthyl or optionally substituted naphthyl, the following being mentioned as substituents: fluorine, chlorine, bromine, iodine, hydroxy, methyl, ethyl, methodoxy, ethoxy, allyloxy, propargyloxy or acetoxy; or is cycloalkyl or cycloalkenyl each of which has 5 to 7 carbon atoms and is optionally substituted by methyl or ethyl, a optionally substituted phenyl, or a radical of the formula

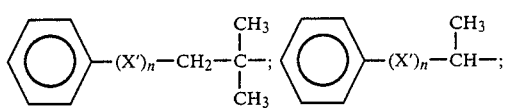

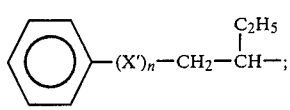

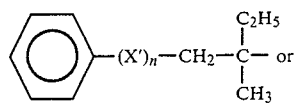

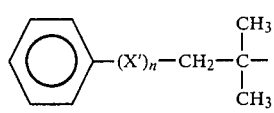

which is optionally substituted in the phenyl nucleus, the following being mentioned as phenyl substituents in each case: hydroxyl, fluorine, chlorine, bromine, iodine, cyano, nitro, methyl, methoxy, methylthio, ethyl, ethoxy, ethylthio, n- or i-propyl, isopropoxy, n-, i-, s- or t-butyl, allyloxy, propargyloxy, trifluoromethyl, trifluoromethoxy, trifluoromethylthio, cyclohexyl, methoxycarbonyl, ethoxycarbonyl or acetoxy, or phenoxy or phenyl which is optionally substituted by fluorine, chlorine or methyl, or the radical R—O—N=CH—, wherein R in each case is methyl, ethyl, n- or i-propyl, n-, i-, s- or t-butyl, allyl or propargyl; or is a radical which is optionally substituted in the cyclohexyl part by methyl, ethyl or isopropyl, of the formula

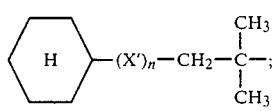

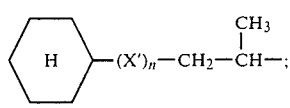

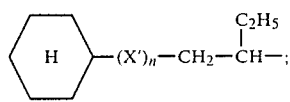

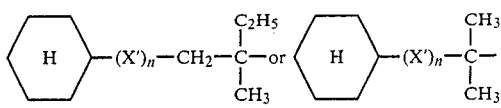

wherein

X' is oxygen or sulphur and n is 0 or 1,

R² is methyl,

R³ is methyl, ethyl, n- or i-propyl and

R⁴ is methyl, ethyl, n- or i-propyl, n-, i-, s- or t-butyl, allyl, but-2-enyl or 3-methylbut-2-enyl, or is benzyl which is optionally monosubstituted to trisubstituted by fluorine, chlorine, methyl and/or trifluoromethyl, or R³ and R⁴, together with the nitrogen atom to which they are bonded, are pyrrolidin-1-yl, piperid-1-yl, piperazin-1-yl, morpholin-4-yl or 1-perhydroazepinyl, each of which is optionally substituted, the following being mentioned as substituents: methyl, ethyl, n- or i-propyl, phenyl, hydroxymethyl, acetoxymethyl, methoxycarbonyloxymethyl, dimethylaminocarbonyloxymethyl, diethylaminocarbonyloxymethyl, methoxyacetoxymethyl or furoyloxymethyl.

4. A compound according to claim 1, wherein such compound is 2-[1-(4-chlorophenoxy)-2-methyl]-prop-2-yl-methyl-5-(3-methyl-piperid-1-ylmethyl)-1,3-oxathiolane of the formula

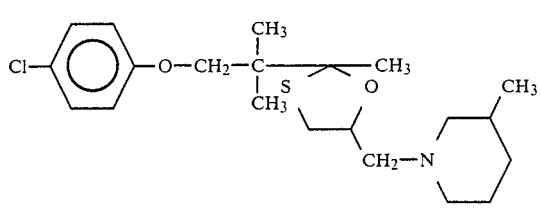

or a plant-tolerated addition product thereof with an acid or metal salt.

5. A compound according to claim 1, wherein such compound is 2-[1-(4-chlorophenoxy)-2-methyl]-prop-2-yl-2-methyl-5-(3,3-dimethyl-piperid-1-ylmethyl)-1,3-oxathiolane of the formula

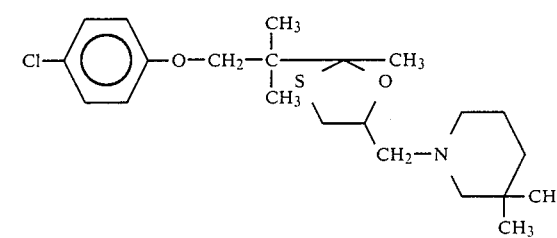

or a plant-tolerated addition product thereof with an acid or metal salt.

6. A compound according to claim 1, wherein such compound is 2-[1-(4-chlorophenoxy)-2-methyl]-prop-2-yl-2-methyl-4-(3,5-dimethylmorpholin-1-ylmethyl)-1,3-oxathiolane of the formula

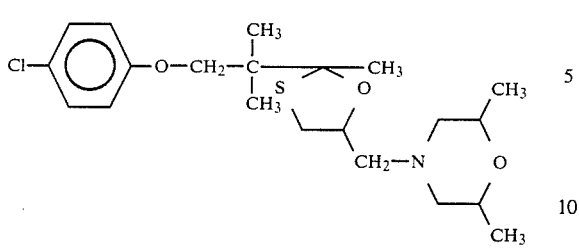

or a plant-tolerated addition product thereof with an acid or metal salt.

7. A compound according to claim 1, wherein such compound is 2-[1-(4-chlorophenoxy)-2-methyl]-prop-2-yl-2-methyl-5-(3-hydroxymethyl-piperid-1-ylmethyl)-1,3-oxathiolane of the formula

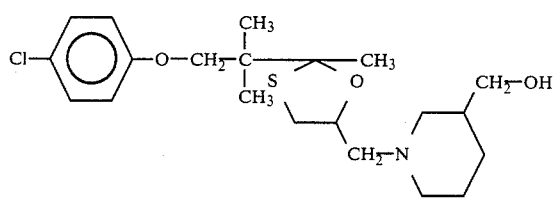

or a plant-tolerated addition product thereof with an acid or metal salt.

8. A compound according to claim 1, wherein such compound is 2-[1-(2,4-dichlorophenoxy)-2-methyl]-prop-2-yl-2-methyl-5-(3-methyl-piperid-1-ylmethyl)-1,3-oxathiolane of the formula

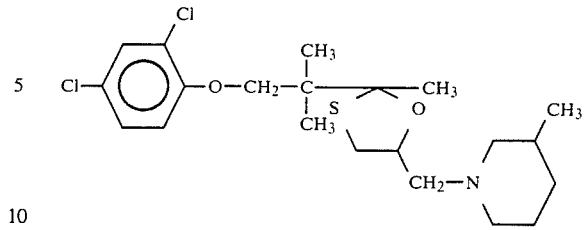

or a plant-tolerated addition product thereof with an acid or metal salt.

9. A microbicidal composition comprising a microbicidally effective amount of a compound or addition product according to claim 1 in admixture with a diluent.

10. A method of combating microorganisms which comprises applying to such microorganisms or to a habitat thereof a microbicidally effective amount of a compound or addition product according to claim 1.

11. The method according to claim 10 wherein such compound is
2-[1-(4-chlorophenoxy)-2-methyl]-prop-2-yl-2-methyl-5-(3-methyl-piperid-1-ylmethyl)-1,3-oxathiolane,
2-[1-(4-chlorophenoxy)-2-methyl]-prop-2-yl-2-methyl-5-(3,3-dimethyl-piperid-1-ylmethyl)-1,3-oxathiolane,
2-[1-(4-chlorophenoxy)-2-methyl]-prop-2-yl-2-methyl-5-(3,5-dimethylmorpholin-1-ylmethyl)-1,3-oxathiolane,
2-[1-(4-chlorophenoxy)-2-methyl]-prop-2-yl-2-methyl-5-(3-hydroxymethyl-piperid-1-ylmethyl)-1,3-oxathiolane or
2-[1-(2,4-dichlorophenoxy)-2-methyl]-prop-2-yl-2-methyl-5-(3-methyl-piperid-1-ylmethyl)-1,3-oxathiolane,
or a plant-tolerated addition product thereof with an acid or metal salt.

* * * * *

UNITED STATES PATENT AND TRADEMARK OFFICE
CERTIFICATE OF CORRECTION

PATENT NO. : 4,542,130
DATED : September 17, 1985
INVENTOR(S) : Joachim Weissmuller, et al.

It is certified that error appears in the above-identified patent and that said Letters Patent is hereby corrected as shown below:

| | |
|---|---|
| Abstract, line 1 | Delete "MIcrobicidally" and substitute --Microbicidally-- |
| Col. 19, line 63 | Correct spelling of "sulphonyl" |
| Col. 21, line 39 | Correct spelling of "example" |
| Col. 24, line 11 | Delete "2-(1-[4-" and substitute --2-[1-(4-  -- |
| Col. 33, line 29 | Delete "12 5" and substitute --12.5-- |
| Col. 33, line 30 | Delete oF" and substitute --of-- |
| Col. 35, lines 48, 49 | Delete "proparcyl" and substitute --propargyl-- |
| Col. 36, line 32 | After "2-yl-" insert --2-- |
| Col. 36, line 67 | After "2-methyl-" delete "4-" and substitute -- 5- -- |

Signed and Sealed this

Twenty-eighth Day of January 1986

[SEAL]

Attest:

DONALD J. QUIGG

Attesting Officer  Commissioner of Patents and Trademarks